US008532807B2

(12) United States Patent
Metzger

(10) Patent No.: US 8,532,807 B2
(45) Date of Patent: Sep. 10, 2013

(54) PRE-OPERATIVE PLANNING AND MANUFACTURING METHOD FOR ORTHOPEDIC PROCEDURE

(75) Inventor: Robert Metzger, Wakarusa, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 239 days.

(21) Appl. No.: 13/153,760

(22) Filed: Jun. 6, 2011

(65) Prior Publication Data

US 2012/0310399 A1  Dec. 6, 2012

(51) Int. Cl.
| G06F 19/00 | (2011.01) |
| G06T 17/00 | (2006.01) |
| G09G 5/00 | (2006.01) |
| A61F 2/46 | (2006.01) |
| A61F 2/30 | (2006.01) |
| A61B 17/88 | (2006.01) |

(52) U.S. Cl.
USPC ............ 700/98; 345/420; 345/629; 606/86 R; 606/281; 623/18.11

(58) Field of Classification Search
USPC ............... 700/95, 97, 98; 345/418–420, 619, 345/629, 630, 634; 606/53, 60, 86 A, 86 B, 606/86 R, 87–90, 96, 280, 281; 623/11.11, 623/13.11, 13.12, 16.11, 18.11, 20.11, 20.14, 623/20.21, 20.32, 20.35, 22.11, 23.39
See application file for complete search history.

(56) References Cited

U.S. PATENT DOCUMENTS

| 1,480,285 A | 1/1924 | Moore |
| 2,181,746 A | 11/1939 | Siebrandt |
| 2,407,845 A | 9/1946 | Nemeyer |
| 2,618,913 A | 11/1952 | Plancon et al. |

(Continued)

FOREIGN PATENT DOCUMENTS

| CA | 2447694 A1 | 12/2002 |
| CA | 2501041 A1 | 4/2004 |

(Continued)

OTHER PUBLICATIONS

K. Subburaj et al., "Automated 3D Geometric Reasoning in Computer Assisted Joint Reconstructive Surgery", IEEE International Conference on Automation Science and Engineering, Publication Year: 2009, pp. 367-372.*

(Continued)

*Primary Examiner* — Crystal J Barnes-Bullock
(74) *Attorney, Agent, or Firm* — Harness, Dickey

(57) ABSTRACT

A pre-operative planning and manufacturing method for orthopedic surgery includes obtaining pre-operative medical image data representing a joint portion of a patient. The method also includes constructing a three-dimensional digital model of the joint portion and manufacturing a patient-specific alignment guide for the joint portion from the three-dimensional digital model of the joint portion when the image data is sufficient to construct the three-dimensional digital model of the joint portion. The patient-specific alignment guide has a three-dimensional patient-specific surface pre-operatively configured to nest and closely conform to a corresponding surface of the joint portion of the patient in only one position relative to the joint portion. The method further includes determining, from the image data, a size of a non-custom implant to be implanted in the patient and manufacturing the non-custom implant when there is insufficient image data to construct the patient-specific alignment guide therefrom.

20 Claims, 5 Drawing Sheets

(56) References Cited

U.S. PATENT DOCUMENTS

| | | |
|---|---|---|
| 2,910,978 A | 11/1959 | Urist |
| 3,840,904 A | 10/1974 | Tronzo |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,475,549 A | 10/1984 | Oh |
| 4,506,393 A | 3/1985 | Murphy |
| 4,524,766 A | 6/1985 | Petersen |
| 4,529,080 A | 7/1985 | Dolan |
| 4,531,623 A | 7/1985 | Arai et al. |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,721,104 A | 1/1988 | Kaufman et al. |
| 4,722,330 A | 2/1988 | Russell et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,027,672 A | 7/1991 | Salvatori et al. |
| 5,030,221 A | 7/1991 | Buechel et al. |
| 5,041,117 A | 8/1991 | Engelhardt |
| 5,053,037 A | 10/1991 | Lackey |
| 5,053,039 A | 10/1991 | Hofmann et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,246,444 A | 9/1993 | Schreiber |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,463,911 A | 11/1995 | Knoedel et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,658,294 A | 8/1997 | Sederholm |
| 5,662,656 A | 9/1997 | White |
| 5,671,018 A | 9/1997 | Ohara et al. |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,826,462 A | 10/1998 | Schaefer |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,033,415 A | 3/2000 | Mittelstadt et al. |
| 6,059,789 A | 5/2000 | Dinger et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,136,033 A | 10/2000 | Suemer |
| 6,156,069 A | 12/2000 | Amstutz |

| Patent No. | Kind | Date | Inventor |
|---|---|---|---|
| 6,161,080 | A | 12/2000 | Aouni-Ateshian et al. |
| 6,164,151 | A | 12/2000 | Dutson et al. |
| 6,187,010 | B1 | 2/2001 | Masini |
| 6,195,615 | B1 | 2/2001 | Lysen |
| 6,203,546 | B1 | 3/2001 | MacMahon |
| 6,205,411 | B1 | 3/2001 | DiGioia, III et al. |
| 6,206,927 | B1 | 3/2001 | Fell et al. |
| 6,254,604 | B1 | 7/2001 | Howell |
| 6,258,097 | B1 | 7/2001 | Cook et al. |
| 6,264,698 | B1 | 7/2001 | Lawes et al. |
| 6,273,891 | B1 | 8/2001 | Masini |
| 6,290,727 | B1 | 9/2001 | Otto et al. |
| 6,293,971 | B1 | 9/2001 | Nelson et al. |
| 6,312,258 | B1 | 11/2001 | Ashman |
| 6,312,473 | B1 | 11/2001 | Oshida |
| 6,319,285 | B1 | 11/2001 | Chamier et al. |
| 6,325,829 | B1 | 12/2001 | Schmotzer |
| 6,343,987 | B2 | 2/2002 | Hayama et al. |
| 6,354,011 | B1 | 3/2002 | Albrecht |
| 6,379,299 | B1 | 4/2002 | Borodulin et al. |
| 6,383,228 | B1 | 5/2002 | Schmotzer |
| 6,391,251 | B1 | 5/2002 | Keicher et al. |
| 6,395,005 | B1 | 5/2002 | Lovell |
| 6,424,332 | B1 * | 7/2002 | Powell ......................... 345/156 |
| 6,427,698 | B1 | 8/2002 | Yoon |
| 6,459,948 | B1 | 10/2002 | Ateshian et al. |
| 6,463,351 | B1 | 10/2002 | Clynch |
| 6,475,243 | B1 | 11/2002 | Sheldon et al. |
| 6,482,236 | B2 | 11/2002 | Habecker |
| 6,488,715 | B1 | 12/2002 | Pope et al. |
| 6,503,255 | B1 | 1/2003 | Albrektsson et al. |
| 6,510,334 | B1 | 1/2003 | Schuster et al. |
| 6,514,259 | B2 | 2/2003 | Picard et al. |
| 6,517,583 | B1 | 2/2003 | Pope et al. |
| 6,520,964 | B2 | 2/2003 | Tallarida et al. |
| 6,533,737 | B1 | 3/2003 | Brosseau et al. |
| 6,547,823 | B2 | 4/2003 | Scarborough et al. |
| 6,554,837 | B1 | 4/2003 | Hauri et al. |
| 6,556,008 | B2 | 4/2003 | Thesen |
| 6,558,391 | B2 | 5/2003 | Axelson, Jr. et al. |
| 6,558,428 | B2 | 5/2003 | Park |
| 6,564,085 | B2 | 5/2003 | Meaney et al. |
| 6,567,681 | B1 | 5/2003 | Lindequist |
| 6,575,980 | B1 | 6/2003 | Robie et al. |
| 6,575,982 | B1 | 6/2003 | Bonutti |
| 6,591,581 | B2 | 7/2003 | Schmieding |
| 6,605,293 | B1 | 8/2003 | Giordano et al. |
| 6,619,153 | B2 | 9/2003 | Smith et al. |
| 6,622,567 | B1 | 9/2003 | Hamel et al. |
| 6,629,999 | B1 | 10/2003 | Serafin, Jr. |
| 6,641,617 | B1 | 11/2003 | Merrill et al. |
| 6,682,566 | B2 | 1/2004 | Draenert |
| 6,696,073 | B2 | 2/2004 | Boyce et al. |
| 6,697,664 | B2 | 2/2004 | Kienzle, III et al. |
| 6,701,174 | B1 | 3/2004 | Krause et al. |
| 6,709,462 | B2 | 3/2004 | Hanssen |
| 6,711,431 | B2 | 3/2004 | Sarin et al. |
| 6,711,432 | B2 | 3/2004 | Krause et al. |
| 6,712,856 | B1 | 3/2004 | Carignan et al. |
| 6,716,249 | B2 | 4/2004 | Hyde |
| 6,725,077 | B1 | 4/2004 | Balloni et al. |
| 6,738,657 | B1 | 5/2004 | Franklin et al. |
| 6,740,092 | B2 | 5/2004 | Lombardo et al. |
| 6,749,638 | B1 | 6/2004 | Saladino |
| 6,750,653 | B1 | 6/2004 | Zou et al. |
| 6,772,026 | B2 | 8/2004 | Bradbury et al. |
| 6,780,190 | B2 | 8/2004 | Maroney |
| 6,786,930 | B2 | 9/2004 | Biscup |
| 6,799,066 | B2 | 9/2004 | Steines et al. |
| 6,823,871 | B2 | 11/2004 | Schmieding |
| 6,827,723 | B2 | 12/2004 | Carson |
| 6,887,247 | B1 | 5/2005 | Couture et al. |
| 6,905,514 | B2 | 6/2005 | Carignan et al. |
| 6,923,817 | B2 | 8/2005 | Carson et al. |
| 6,923,831 | B2 | 8/2005 | Fell et al. |
| 6,932,842 | B1 | 8/2005 | Litschko et al. |
| 6,942,475 | B2 | 9/2005 | Ensign et al. |
| 6,944,518 | B2 | 9/2005 | Roose |
| 6,945,976 | B2 | 9/2005 | Ball et al. |
| 6,953,480 | B2 | 10/2005 | Mears et al. |
| 6,960,216 | B2 | 11/2005 | Kolb et al. |
| 6,990,220 | B2 | 1/2006 | Ellis et al. |
| 7,029,479 | B2 | 4/2006 | Tallarida et al. |
| 7,042,222 | B2 | 5/2006 | Zheng et al. |
| 7,048,741 | B2 | 5/2006 | Swanson |
| 7,050,877 | B2 | 5/2006 | Iseki et al. |
| 7,060,074 | B2 | 6/2006 | Rosa et al. |
| 7,074,241 | B2 | 7/2006 | McKinnon |
| RE39,301 | E | 9/2006 | Bertin |
| 7,104,997 | B2 | 9/2006 | Lionberger et al. |
| 7,105,026 | B2 | 9/2006 | Johnson et al. |
| 7,115,131 | B2 | 10/2006 | Engh et al. |
| 7,141,053 | B2 | 11/2006 | Rosa et al. |
| 7,169,185 | B2 | 1/2007 | Sidebotham |
| 7,176,466 | B2 | 2/2007 | Rousso et al. |
| 7,184,814 | B2 | 2/2007 | Lang et al. |
| 7,198,628 | B2 | 4/2007 | Ondrla et al. |
| 7,218,232 | B2 | 5/2007 | DiSilvestro et al. |
| 7,239,908 | B1 | 7/2007 | Alexander et al. |
| 7,241,315 | B2 | 7/2007 | Evans |
| 7,255,702 | B2 | 8/2007 | Serra et al. |
| 7,258,701 | B2 | 8/2007 | Aram et al. |
| 7,275,218 | B2 | 9/2007 | Petrella et al. |
| 7,282,054 | B2 | 10/2007 | Steffensmeier et al. |
| 7,294,133 | B2 | 11/2007 | Zink et al. |
| 7,297,164 | B2 | 11/2007 | Johnson et al. |
| 7,309,339 | B2 | 12/2007 | Cusick et al. |
| 7,333,013 | B2 | 2/2008 | Berger |
| 7,335,231 | B2 | 2/2008 | McLean |
| 7,371,260 | B2 | 5/2008 | Malinin |
| 7,383,164 | B2 | 6/2008 | Aram et al. |
| 7,385,498 | B2 | 6/2008 | Dobosz |
| 7,388,972 | B2 | 6/2008 | Kitson |
| 7,392,076 | B2 | 6/2008 | Moctezuma de La Barrera |
| 7,427,200 | B2 | 9/2008 | Noble et al. |
| 7,427,272 | B2 | 9/2008 | Richard et al. |
| 7,468,075 | B2 | 12/2008 | Lang et al. |
| 7,474,223 | B2 | 1/2009 | Nycz et al. |
| 7,488,325 | B2 | 2/2009 | Qian |
| 7,494,510 | B2 | 2/2009 | Zweymuller |
| 7,517,365 | B2 | 4/2009 | Carignan et al. |
| 7,527,631 | B2 | 5/2009 | Maroney et al. |
| 7,534,263 | B2 | 5/2009 | Burdulis, Jr. et al. |
| 7,542,791 | B2 | 6/2009 | Mire et al. |
| 7,559,931 | B2 | 7/2009 | Stone |
| 7,575,602 | B2 | 8/2009 | Amirouche et al. |
| 7,578,851 | B2 | 8/2009 | Dong et al. |
| 7,582,091 | B2 | 9/2009 | Duncan et al. |
| 7,591,821 | B2 | 9/2009 | Kelman |
| 7,601,155 | B2 | 10/2009 | Petersen |
| 7,604,639 | B2 | 10/2009 | Swanson |
| 7,611,516 | B2 | 11/2009 | Maroney |
| 7,618,451 | B2 | 11/2009 | Berez et al. |
| 7,621,915 | B2 | 11/2009 | Frederick et al. |
| 7,625,409 | B2 | 12/2009 | Saltzman et al. |
| 7,646,161 | B2 | 1/2010 | Albu-Schaffer et al. |
| 7,651,501 | B2 | 1/2010 | Penenberg et al. |
| 7,670,345 | B2 | 3/2010 | Plassky et al. |
| 7,682,398 | B2 | 3/2010 | Croxton et al. |
| 7,695,477 | B2 | 4/2010 | Creger et al. |
| 7,695,521 | B2 | 4/2010 | Ely et al. |
| 7,699,847 | B2 | 4/2010 | Sheldon et al. |
| 7,704,253 | B2 | 4/2010 | Bastian et al. |
| 7,723,395 | B2 | 5/2010 | Ringeisen et al. |
| 7,780,672 | B2 | 8/2010 | Metzger et al. |
| 7,780,740 | B2 | 8/2010 | Steinberg |
| 7,794,466 | B2 | 9/2010 | Merchant et al. |
| 7,794,467 | B2 | 9/2010 | McGinley et al. |
| 7,794,504 | B2 | 9/2010 | Case |
| 7,806,896 | B1 | 10/2010 | Bonutti |
| 7,809,184 | B2 | 10/2010 | Neubauer et al. |
| 7,819,925 | B2 | 10/2010 | King et al. |
| 7,828,806 | B2 | 11/2010 | Graf et al. |
| 7,879,109 | B2 | 2/2011 | Borden et al. |
| 7,892,261 | B2 | 2/2011 | Bonutti |
| 7,896,921 | B2 | 3/2011 | Smith et al. |
| 7,935,119 | B2 | 5/2011 | Ammann et al. |
| 7,935,150 | B2 | 5/2011 | Carignan et al. |

| | | | | | | |
|---|---|---|---|---|---|---|
| 7,938,861 B2 | 5/2011 | King et al. | 2004/0172137 A1 | 9/2004 | Blaylock et al. |
| 7,959,637 B2 | 6/2011 | Fox et al. | 2004/0181144 A1 | 9/2004 | Cinquin et al. |
| 7,962,196 B2 | 6/2011 | Tuma | 2004/0204644 A1 | 10/2004 | Tsougarakis et al. |
| 7,963,968 B2 | 6/2011 | Dees, Jr. | 2004/0204760 A1 | 10/2004 | Fitz et al. |
| 7,967,823 B2 | 6/2011 | Ammann et al. | 2004/0212586 A1 | 10/2004 | Denny |
| 7,967,868 B2 | 6/2011 | White et al. | 2004/0220583 A1 | 11/2004 | Pieczynski et al. |
| 7,974,677 B2 | 7/2011 | Mire et al. | 2004/0236341 A1 | 11/2004 | Petersen |
| 7,981,158 B2 | 7/2011 | Fitz et al. | 2004/0236424 A1 | 11/2004 | Berez et al. |
| 7,993,353 B2 | 8/2011 | Rossner et al. | 2004/0243481 A1 | 12/2004 | Bradbury et al. |
| 8,062,301 B2 | 11/2011 | Ammann et al. | 2004/0254584 A1 | 12/2004 | Sarin et al. |
| 8,070,752 B2 | 12/2011 | Metzger et al. | 2004/0260301 A1 | 12/2004 | Lionberger et al. |
| 8,083,745 B2 | 12/2011 | Lang et al. | 2005/0008887 A1 | 1/2005 | Haymann et al. |
| 8,083,746 B2 | 12/2011 | Novak | 2005/0010227 A1 | 1/2005 | Paul |
| 8,083,749 B2 | 12/2011 | Taber | 2005/0010300 A1 | 1/2005 | Disilvestro et al. |
| 8,086,336 B2 | 12/2011 | Christensen | 2005/0015022 A1 | 1/2005 | Richard et al. |
| 8,092,465 B2 | 1/2012 | Metzger et al. | 2005/0019664 A1 | 1/2005 | Matsumoto |
| 8,133,230 B2 | 3/2012 | Stevens et al. | 2005/0027303 A1 | 2/2005 | Lionberger et al. |
| 8,133,234 B2 | 3/2012 | Meridew et al. | 2005/0027361 A1 | 2/2005 | Reiley |
| 8,137,406 B2 | 3/2012 | Novak et al. | 2005/0043806 A1 | 2/2005 | Cook et al. |
| 8,167,951 B2 | 5/2012 | Ammann et al. | 2005/0043837 A1 | 2/2005 | Rubbert et al. |
| 8,170,641 B2 | 5/2012 | Belcher | 2005/0049524 A1 | 3/2005 | Lefevre et al. |
| 8,182,489 B2 | 5/2012 | Horacek | 2005/0049603 A1 | 3/2005 | Calton et al. |
| 8,192,441 B2 | 6/2012 | Collazo | 2005/0059873 A1 | 3/2005 | Glozman et al. |
| 8,211,112 B2 | 7/2012 | Novak et al. | 2005/0060040 A1 | 3/2005 | Auxepaules et al. |
| 8,241,292 B2 | 8/2012 | Collazo | 2005/0065628 A1 | 3/2005 | Roose |
| 8,241,293 B2 | 8/2012 | Stone et al. | 2005/0070897 A1 | 3/2005 | Petersen |
| 8,265,790 B2 | 9/2012 | Amiot et al. | 2005/0071015 A1 | 3/2005 | Sekel |
| 8,282,646 B2 | 10/2012 | Schoenefeld et al. | 2005/0075641 A1 | 4/2005 | Singhatat et al. |
| 8,298,237 B2 | 10/2012 | Schoenefeld et al. | 2005/0096535 A1 | 5/2005 | de la Barrera |
| 8,303,596 B2 | 11/2012 | Plaßky et al. | 2005/0113841 A1 | 5/2005 | Sheldon et al. |
| 8,333,772 B2 | 12/2012 | Fox et al. | 2005/0113846 A1 | 5/2005 | Carson |
| 2001/0005797 A1 | 6/2001 | Barlow et al. | 2005/0119664 A1 | 6/2005 | Carignan et al. |
| 2001/0011190 A1 | 8/2001 | Park | 2005/0131662 A1 | 6/2005 | Ascenzi et al. |
| 2001/0054478 A1 | 12/2001 | Watanabe et al. | 2005/0137708 A1 | 6/2005 | Clark |
| 2002/0007294 A1 | 1/2002 | Bradbury et al. | 2005/0148843 A1 | 7/2005 | Roose |
| 2002/0029045 A1 | 3/2002 | Bonutti | 2005/0149042 A1 | 7/2005 | Metzger |
| 2002/0052606 A1 | 5/2002 | Bonutti | 2005/0171545 A1 | 8/2005 | Walsh et al. |
| 2002/0059049 A1 | 5/2002 | Bradbury et al. | 2005/0177245 A1 | 8/2005 | Leatherbury et al. |
| 2002/0082741 A1 | 6/2002 | Mazumder et al. | 2005/0203536 A1 | 9/2005 | Laffargue et al. |
| 2002/0087274 A1 | 7/2002 | Alexander et al. | 2005/0203540 A1 | 9/2005 | Broyles |
| 2002/0107522 A1 | 8/2002 | Picard et al. | 2005/0216305 A1 | 9/2005 | Funderud |
| 2002/0128872 A1 | 9/2002 | Giammattei | 2005/0222573 A1 | 10/2005 | Branch et al. |
| 2002/0147415 A1 | 10/2002 | Martelli | 2005/0228393 A1 | 10/2005 | Williams et al. |
| 2003/0009171 A1 | 1/2003 | Tornier | 2005/0234461 A1 | 10/2005 | Burdulis et al. |
| 2003/0009234 A1 | 1/2003 | Treacy et al. | 2005/0234468 A1 | 10/2005 | Carson |
| 2003/0011624 A1 | 1/2003 | Ellis | 2005/0240195 A1 | 10/2005 | Axelson et al. |
| 2003/0018338 A1 | 1/2003 | Axelson et al. | 2005/0240267 A1 | 10/2005 | Randall et al. |
| 2003/0039676 A1 | 2/2003 | Boyce et al. | 2005/0244239 A1 | 11/2005 | Shimp |
| 2003/0055502 A1 | 3/2003 | Lang et al. | 2005/0245934 A1 | 11/2005 | Tuke et al. |
| 2003/0105526 A1 | 6/2003 | Bryant et al. | 2005/0245936 A1 | 11/2005 | Tuke et al. |
| 2003/0109784 A1 | 6/2003 | Loh et al. | 2005/0251147 A1 | 11/2005 | Novak |
| 2003/0120276 A1 | 6/2003 | Tallarida et al. | 2005/0267353 A1 | 12/2005 | Marquart et al. |
| 2003/0139817 A1 | 7/2003 | Tuke et al. | 2005/0267485 A1 | 12/2005 | Cordes et al. |
| 2003/0158606 A1 | 8/2003 | Coon et al. | 2005/0267584 A1 | 12/2005 | Burdulis et al. |
| 2003/0171757 A1 | 9/2003 | Coon et al. | 2005/0273114 A1 | 12/2005 | Novak |
| 2003/0216669 A1 | 11/2003 | Lang et al. | 2005/0283252 A1 | 12/2005 | Coon et al. |
| 2004/0018144 A1 | 1/2004 | Briscoe | 2005/0283253 A1 | 12/2005 | Coon et al. |
| 2004/0030245 A1 | 2/2004 | Noble et al. | 2006/0004284 A1 | 1/2006 | Grunschlager et al. |
| 2004/0054372 A1 | 3/2004 | Corden et al. | 2006/0015120 A1 | 1/2006 | Richard et al. |
| 2004/0068187 A1 | 4/2004 | Krause et al. | 2006/0030853 A1 | 2/2006 | Haines |
| 2004/0092932 A1 | 5/2004 | Aubin et al. | 2006/0038520 A1 | 2/2006 | Negoro et al. |
| 2004/0098133 A1 | 5/2004 | Carignan et al. | 2006/0052725 A1 | 3/2006 | Santilli |
| 2004/0102852 A1 | 5/2004 | Johnson et al. | 2006/0058803 A1 | 3/2006 | Cuckler et al. |
| 2004/0102866 A1 | 5/2004 | Harris et al. | 2006/0058884 A1 | 3/2006 | Aram et al. |
| 2004/0106926 A1 | 6/2004 | Leitner et al. | 2006/0058886 A1 | 3/2006 | Wozencroft |
| 2004/0115586 A1 | 6/2004 | Andreiko et al. | 2006/0089621 A1 | 4/2006 | Fard |
| 2004/0122439 A1 | 6/2004 | Dwyer et al. | 2006/0093988 A1 | 5/2006 | Swaelens et al. |
| 2004/0128026 A1 | 7/2004 | Harris et al. | 2006/0094951 A1 | 5/2006 | Dean et al. |
| 2004/0133276 A1 | 7/2004 | Lang et al. | 2006/0095044 A1 | 5/2006 | Grady et al. |
| 2004/0138754 A1 | 7/2004 | Lang et al. | 2006/0100832 A1 | 5/2006 | Bowman |
| 2004/0143336 A1 | 7/2004 | Burkinshaw | 2006/0111722 A1 | 5/2006 | Bouadi |
| 2004/0147927 A1 | 7/2004 | Tsougarakis et al. | 2006/0122616 A1 | 6/2006 | Bennett et al. |
| 2004/0148026 A1 | 7/2004 | Bonutti | 2006/0136058 A1 | 6/2006 | Pietrzak |
| 2004/0153079 A1 | 8/2004 | Tsougarakis et al. | 2006/0142657 A1 | 6/2006 | Quaid et al. |
| 2004/0153087 A1 | 8/2004 | Sanford et al. | 2006/0155380 A1 | 7/2006 | Clemow et al. |
| 2004/0158254 A1 | 8/2004 | Eisermann | 2006/0161167 A1 | 7/2006 | Myers et al. |
| 2004/0162619 A1 | 8/2004 | Blaylock et al. | 2006/0172263 A1 | 8/2006 | Quadling et al. |
| 2004/0167390 A1 | 8/2004 | Alexander et al. | 2006/0178497 A1 | 8/2006 | Gevaert et al. |
| 2004/0171924 A1 | 9/2004 | Mire et al. | 2006/0184177 A1 | 8/2006 | Echeverri |

| | | |
|---|---|---|
| 2006/0184250 A1 | 8/2006 | Bandoh et al. |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |

| | | | | | |
|---|---|---|---|---|---|
| 2009/0118736 A1 | 5/2009 | Kreuzer | 2010/0305574 A1 | 12/2010 | Fitz et al. |
| 2009/0118769 A1 | 5/2009 | Sixto, Jr. et al. | 2010/0318088 A1 | 12/2010 | Warne et al. |
| 2009/0131941 A1 | 5/2009 | Park et al. | 2010/0324692 A1 | 12/2010 | Uthgenannt et al. |
| 2009/0131942 A1 | 5/2009 | Aker et al. | 2011/0004317 A1 | 1/2011 | Hacking et al. |
| 2009/0138020 A1 | 5/2009 | Park et al. | 2011/0009869 A1 | 1/2011 | Marino et al. |
| 2009/0149965 A1 | 6/2009 | Quaid | 2011/0015636 A1 | 1/2011 | Katrana et al. |
| 2009/0149977 A1 | 6/2009 | Schendel | 2011/0015639 A1 | 1/2011 | Metzger et al. |
| 2009/0151736 A1 | 6/2009 | Belcher et al. | 2011/0015752 A1 | 1/2011 | Meridew |
| 2009/0157083 A1 | 6/2009 | Park et al. | 2011/0022049 A1 | 1/2011 | Huebner et al. |
| 2009/0163922 A1 | 6/2009 | Meridew et al. | 2011/0029091 A1 | 2/2011 | Bojarski et al. |
| 2009/0163923 A1 | 6/2009 | Flett et al. | 2011/0029093 A1* | 2/2011 | Bojarski et al. ............ 623/20.35 |
| 2009/0164024 A1 | 6/2009 | Rudan et al. | 2011/0029116 A1 | 2/2011 | Jordan et al. |
| 2009/0177282 A1 | 7/2009 | Bureau et al. | 2011/0035012 A1 | 2/2011 | Linares |
| 2009/0187193 A1 | 7/2009 | Maroney et al. | 2011/0040303 A1 | 2/2011 | Iannotti |
| 2009/0209884 A1 | 8/2009 | Van Vorhis et al. | 2011/0040334 A1 | 2/2011 | Kaes et al. |
| 2009/0209961 A1 | 8/2009 | Ferrante et al. | 2011/0046735 A1 | 2/2011 | Metzger et al. |
| 2009/0222014 A1 | 9/2009 | Bojarski et al. | 2011/0054478 A1 | 3/2011 | Vanasse et al. |
| 2009/0222015 A1 | 9/2009 | Park et al. | 2011/0066193 A1 | 3/2011 | Lang et al. |
| 2009/0222016 A1 | 9/2009 | Park et al. | 2011/0066245 A1 | 3/2011 | Lang et al. |
| 2009/0222103 A1 | 9/2009 | Fitz et al. | 2011/0071528 A1 | 3/2011 | Carson |
| 2009/0226068 A1 | 9/2009 | Fitz et al. | 2011/0071529 A1 | 3/2011 | Carson |
| 2009/0228016 A1 | 9/2009 | Alvarez | 2011/0071530 A1 | 3/2011 | Carson |
| 2009/0234360 A1 | 9/2009 | Alexander | 2011/0071532 A1 | 3/2011 | Carson |
| 2009/0248044 A1 | 10/2009 | Amiot et al. | 2011/0071533 A1 | 3/2011 | Metzger et al. |
| 2009/0254093 A1 | 10/2009 | White et al. | 2011/0092804 A1 | 4/2011 | Schoenefeld et al. |
| 2009/0254367 A1 | 10/2009 | Belcher et al. | 2011/0093086 A1 | 4/2011 | Witt et al. |
| 2009/0259312 A1 | 10/2009 | Shterling et al. | 2011/0106254 A1 | 5/2011 | Abel et al. |
| 2009/0270868 A1 | 10/2009 | Park et al. | 2011/0125264 A1 | 5/2011 | Bagga et al. |
| 2009/0274350 A1 | 11/2009 | Pavlovskaia et al. | 2011/0130795 A1 | 6/2011 | Ball |
| 2009/0287217 A1 | 11/2009 | Ammann et al. | 2011/0151027 A1 | 6/2011 | Clineff et al. |
| 2009/0306676 A1 | 12/2009 | Lang et al. | 2011/0151259 A1 | 6/2011 | Jarman-Smith et al. |
| 2009/0307893 A1 | 12/2009 | Burdulis, Jr. et al. | 2011/0153025 A1 | 6/2011 | McMinn |
| 2009/0318836 A1 | 12/2009 | Stone et al. | 2011/0160736 A1 | 6/2011 | Meridew et al. |
| 2009/0318921 A1 | 12/2009 | White et al. | 2011/0160867 A1 | 6/2011 | Meridew et al. |
| 2010/0010493 A1 | 1/2010 | Dower | 2011/0166578 A1 | 7/2011 | Stone et al. |
| 2010/0016984 A1 | 1/2010 | Trabish | 2011/0172672 A1 | 7/2011 | Dubeau et al. |
| 2010/0016986 A1 | 1/2010 | Trabish | 2011/0184419 A1 | 7/2011 | Meridew et al. |
| 2010/0023015 A1 | 1/2010 | Park | 2011/0184526 A1 | 7/2011 | White et al. |
| 2010/0030231 A1 | 2/2010 | Revie et al. | 2011/0190899 A1 | 8/2011 | Pierce et al. |
| 2010/0042105 A1 | 2/2010 | Park et al. | 2011/0190901 A1 | 8/2011 | Weissberg et al. |
| 2010/0049195 A1 | 2/2010 | Park et al. | 2011/0213376 A1 | 9/2011 | Maxson et al. |
| 2010/0057088 A1 | 3/2010 | Shah | 2011/0214279 A1 | 9/2011 | Park et al. |
| 2010/0076439 A1 | 3/2010 | Hatch | 2011/0218545 A1 | 9/2011 | Catanzarite et al. |
| 2010/0076505 A1 | 3/2010 | Borja | 2011/0224674 A1 | 9/2011 | White et al. |
| 2010/0076563 A1 | 3/2010 | Otto et al. | 2011/0251617 A1 | 10/2011 | Ammann et al. |
| 2010/0076571 A1 | 3/2010 | Hatch | 2011/0257657 A1 | 10/2011 | Turner et al. |
| 2010/0082034 A1 | 4/2010 | Remia | 2011/0269100 A1 | 11/2011 | Furrer et al. |
| 2010/0082035 A1 | 4/2010 | Keefer | 2011/0275032 A1 | 11/2011 | Tardieu et al. |
| 2010/0087829 A1 | 4/2010 | Metzger et al. | 2012/0010619 A1 | 1/2012 | Barsoum |
| 2010/0094295 A1 | 4/2010 | Schnieders et al. | 2012/0010710 A1 | 1/2012 | Frigg |
| 2010/0105011 A1 | 4/2010 | Karkar et al. | 2012/0010711 A1 | 1/2012 | Antonyshyn et al. |
| 2010/0121334 A1 | 5/2010 | Couture et al. | 2012/0041446 A1* | 2/2012 | Wong et al. .................... 606/96 |
| 2010/0121335 A1 | 5/2010 | Penenberg et al. | 2012/0065640 A1 | 3/2012 | Metzger et al. |
| 2010/0137869 A1 | 6/2010 | Borja et al. | 2012/0078259 A1 | 3/2012 | Meridew |
| 2010/0137924 A1 | 6/2010 | Tuke et al. | 2012/0089595 A1 | 4/2012 | Jaecksch |
| 2010/0145343 A1 | 6/2010 | Johnson et al. | 2012/0101586 A1 | 4/2012 | Carson |
| 2010/0145344 A1 | 6/2010 | Jordan et al. | 2012/0109137 A1 | 5/2012 | Iannotti et al. |
| 2010/0152782 A1 | 6/2010 | Stone et al. | 2012/0109138 A1 | 5/2012 | Meridew et al. |
| 2010/0160917 A1 | 6/2010 | Fitz et al. | 2012/0109226 A1 | 5/2012 | Iannotti et al. |
| 2010/0168752 A1 | 7/2010 | Edwards | 2012/0130382 A1 | 5/2012 | Iannotti et al. |
| 2010/0168754 A1 | 7/2010 | Fitz et al. | 2012/0136365 A1 | 5/2012 | Iannotti et al. |
| 2010/0168857 A1 | 7/2010 | Hatch | 2012/0141034 A1 | 6/2012 | Iannotti et al. |
| 2010/0179663 A1 | 7/2010 | Steinberg | 2012/0143197 A1 | 6/2012 | Lang et al. |
| 2010/0185202 A1 | 7/2010 | Lester et al. | 2012/0143267 A1 | 6/2012 | Iannotti et al. |
| 2010/0191244 A1 | 7/2010 | White et al. | 2012/0209276 A1 | 8/2012 | Schuster |
| 2010/0198224 A1 | 8/2010 | Metzger et al. | 2012/0215225 A1 | 8/2012 | Philippon et al. |
| 2010/0212138 A1 | 8/2010 | Carroll et al. | 2012/0221017 A1 | 8/2012 | Bonutti |
| 2010/0217109 A1 | 8/2010 | Belcher | 2012/0226283 A1 | 9/2012 | Meridew et al. |
| 2010/0217270 A1 | 8/2010 | Polinski et al. | 2012/0232596 A1 | 9/2012 | Ribeiro |
| 2010/0217336 A1 | 8/2010 | Crawford et al. | 2012/0265208 A1 | 10/2012 | Smith |
| 2010/0217338 A1 | 8/2010 | Carroll et al. | 2012/0271314 A1 | 10/2012 | Stemniski et al. |
| 2010/0228257 A1 | 9/2010 | Bonutti | 2012/0271366 A1 | 10/2012 | Katrana et al. |
| 2010/0249657 A1 | 9/2010 | Nycz et al. | 2012/0277751 A1 | 11/2012 | Catanzarite et al. |
| 2010/0249796 A1 | 9/2010 | Nycz | 2012/0289965 A1 | 11/2012 | Gelaude et al. |
| 2010/0262150 A1 | 10/2010 | Lian | 2012/0296339 A1 | 11/2012 | Iannotti et al. |
| 2010/0274253 A1 | 10/2010 | Ure | 2012/0303004 A1 | 11/2012 | Uthgenannt et al. |
| 2010/0281678 A1 | 11/2010 | Burdulis, Jr. et al. | 2012/0303033 A1 | 11/2012 | Weiner et al. |
| 2010/0286700 A1 | 11/2010 | Snider et al. | 2012/0310399 A1 | 12/2012 | Metzger |
| 2010/0292743 A1 | 11/2010 | Singhal et al. | 2012/0316564 A1 | 12/2012 | Serbousek et al. |

| | | | |
|---|---|---|---|
| 2012/0323246 A1 | 12/2012 | Catanzarite et al. | |
| 2013/0001121 A1 | 1/2013 | Metzger | |
| 2013/0006250 A1 | 1/2013 | Metzger et al. | |
| 2013/0035766 A1 | 2/2013 | Meridew | |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1852072 A2 | 7/2007 |
| EP | 1832239 A1 | 9/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| TW | 201114409 A * | 5/2011 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |

OTHER PUBLICATIONS

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.
International Preliminary Report on Patentability for PCT/US2010/050701 mailed Apr. 12, 2012 claiming benefit of U.S. Appl. No. 12/571,969, filed Oct. 1, 2009.
International Search Report and Written Opinion mailed Mar. 5, 2012 for PCT/US2011/057300 claiming benefit of U.S. Appl. No. 12/938,905, filed Nov. 3, 2010.
International Search Report and Written Opinion mailed May 8, 2012 for PCT/US2012/026356 claiming benefit of U.S. Appl. No. 13/041,883, filed Mar. 7, 2011.
Thoma, W., et al., "Endoprothetischen Versorgung des Kniegelenks auf der Basis eines 3D-computertomographischen Subtraktionsverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).
International Preliminary Report on Patentability mailed Aug. 25, 2011 for PCT/US2010/024073 filed Feb. 12, 2010, claiming benefit of U.S. Appl. No. 12/371,096, filed Feb. 13, 2009.
International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Search Report and Written Opinion mailed Aug. 9, 2011 for PCT/US2011/026333 claiming benefit of U.S. Appl. No. 12/714,023, filed Feb. 26, 2010.
"Comprehensive® Reverse Shoulder System Surgical Technique," Biomet Orthopedics brochure (2009-2012), 48 pages.
"Comprehensive® Reverse Shoulder System Technical Design Features," Biomet Orthopedics brochure (2009), 3 pages.
"Comprehensive® Reverse Shoulder System," Biomet Orthopedics brochure (2009), 8 pages.
"Comprehensive® Shoulder System Surgical Technique," Biomet Orthopedics brochure (2007), pp. 1-53.
"Comprehensive® Total Shoulder System," Biomet Orthopedics brochure (2011), 4 pages.
Friedman, R.J. et al., "The Use of Computerized Tomography in the Measurement of Glenoid Version", Journal of Bone & Joint Surgery Am. (JBJS) 1992;74:1032-1037 (Aug. 1992).
International Search Report and Written Opinion mailed Dec. 18, 2012 for PCT/US2012/059189, which claims benefit of U.S. Appl. No. 13/597,478, filed Aug. 29, 2011.
International Search Report and Written Opinion mailed Feb. 6, 2013 for PCT/US2012/060842, which claims benefit of U.S. Appl. No. 13/653,868, filed Oct. 17, 2012.
International Search Report and Written Opinion mailed Feb. 6, 2013 for PCT/US2012/060854, which claims benefit of U.S. Appl. No. 13/653,893, filed Oct. 17, 2012.
International Search Report and Written Opinion mailed Nov. 15, 2012, for PCT/US2012/052853, which claims benefit of U.S. Appl. No. 13/221,968, filed Aug. 31, 2011.
International Search Report mailed Oct. 23, 2012, for PCT/US2012/041893, which claims benefit of U.S. Appl. No. 61/496,177, filed Jun. 13, 2011.
Invitation to Pay Additional Fees mailed Feb. 6, 2013 for PCT/US2012/060848, which claims benefit of U.S. Appl. No. 13/653,878, filed Oct. 17, 2012.
Invitation to Pay Additional Fees mailed Feb. 7, 2013 for PCT/US2012/060853, which claims benefit of U.S. Appl. No. 13/653,893, filed Oct. 17, 2012.
"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (1999) 16 sheets.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (2008) pp. 1-25.
"Discovery® Elbow System," brochure. Biomet Orthopedics, Inc. (2007) 3 sheets.
"Hipsextant Instructions of Use." (2011) Surgical Planning Associates, Inc. 19 pages.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (2003) pp. 1-8 (12 sheets).
"Patient Matched PMI Implants, C.A.M.R.A. 3-D Imaging," brochure, Biomet, Inc. (1990) 6 pages.
"Regenerex® Tibial Cone Augment, Surgical Technique Addendum to the Vanguard® SSK Revision System," brochure. Biomet® Orthopedics. (2009) pp. 1-8 (12 sheets).
"Signature™ Personalized Patient Care, Surgical Technique Addendum to the Vanguard Knee System" brochure. Biomet® Orthopedics, Inc. (2009) pp. 1-8.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (2010) pp. 1-25.
"Zimmer® UniSpacer® Knee System," brochure. (2005) Zimmer, Inc. 4 sheets.
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., 'Technical Report DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive navigiert implantierte unikondyläre Knleendoprothese," Orthopäde 2006 35:1073-1079 (2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756,057, filed May 31, 2007.

International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-baslerte Planung und DISOS-Schablonennavigation in der Kniegelenkendoprothetik," in Navigation und Robotic in der Gelenk—und Wirbelsäulenchlrugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205-1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung und Stereolithographie-Implantatbohrschablonen, Stomatologie 101.3, pp. 55-59 (2004).

Sharp, S. Michael, Ph.D., Patient-Specific, Resurfacing Bi-Compartmental Arthruroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796& ISSUE ... accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Biomet "Oxford® Partial Knee" brochure, 8 pages (Feb. 2011).

Biomet "The Oxford® Partial Knee Surgical Technique," brochure, pp. 1-38, (Feb. 2010).

International Preliminary Report on Patentability and Written Opinion mailed Sep. 7, 2012 for PCT/US2011/026333 claiming benefit of U.S. Appl. No. 12/714,023, filed Feb. 26, 2010.

* cited by examiner

PRE-OPERATIVE PLANNING AND MANUFACTURING METHOD FOR ORTHOPEDIC PROCEDURE

INTRODUCTION

The present teachings provide various methods of pre-operative planning and manufacturing for orthopedic procedures.

SUMMARY

The present teachings provide a pre-operative planning and manufacturing method for orthopedic surgery. The method includes obtaining pre-operative medical image data representing a joint portion of a patient. The method also includes constructing a three-dimensional digital model of the joint portion and manufacturing a patient-specific alignment guide for the joint portion from the three-dimensional digital model of the joint portion when the image data is sufficient to construct the three-dimensional digital model of the joint portion. The patient-specific alignment guide has a three-dimensional patient-specific surface pre-operatively configured to nest and closely conform to a corresponding surface of the joint portion of the patient in only one position relative to the joint portion. The method further includes determining, from the image data, a size of a non-custom implant to be implanted in the patient and manufacturing the non-custom implant when there is insufficient image data to construct the patient-specific alignment guide therefrom.

A pre-operative planning and manufacturing method for orthopedic surgery is also disclosed. The method includes pre-operatively obtaining medical image data that is readable on a computer. The medical image data contains a plurality of two-dimensional medical images of a joint portion of a patient. The method also includes pre-operatively constructing a three-dimensional digital model of the joint portion from the plurality of two-dimensional medical images and displaying the three-dimensional digital model on a display of the computer when the plurality of two-dimensional medical images are sufficient to construct the three-dimensional digital model of the joint portion. Furthermore, the method includes selecting, based on the image data, a non-custom implant to be implanted in the patient and providing the non-custom implant when the plurality of two-dimensional medical images are insufficient for use in constructing a patient-specific alignment guide having a three-dimensional patient-specific surface configured to nest and closely conform to a corresponding surface of the joint portion of the patient in only one position relative to the joint portion. The non-custom implant is chosen from a group of non-custom implants of different sizes.

Moreover, a computerized pre-operative planning tool for planning an orthopedic surgical procedure is disclosed. The tool includes a receiver device that receives medical image data containing a plurality of two-dimensional medical images of a joint portion of a patient. The tool also includes a processor that determines whether the medical image data is sufficient for constructing a three-dimensional digital model of the joint portion from the plurality of two-dimensional medical images. The processor is additionally configured to construct the three-dimensional digital model when the medical image data is sufficient to construct the three-dimensional digital model. The processor is further configured to construct a patient-specific digital model of a patient-specific alignment guide when the medical image data is sufficient to construct the three-dimensional digital model. The patient-specific alignment guide has a three-dimensional surface that nests against a corresponding surface of the three-dimensional digital model of the joint portion. Additionally, the tool includes a display that displays the three-dimensional digital model of the joint portion and the patient specific digital model of the patient-specific alignment guide when the processor determines that the medical image data is sufficient for constructing the three-dimensional digital model of the joint portion. The display also displays at least one of the two-dimensional medical images of the joint portion for selection of a non-custom implant when the processor determines that the medical image data is insufficient for constructing the patient-specific alignment guide therefrom.

Still further, a pre-operative planning and manufacturing method for orthopedic surgery of a knee joint of a patient is disclosed. The method includes obtaining pre-operative medical image data representing the knee joint, wherein the medical image data includes a plurality of two-dimensional images of the knee joint. The method also includes constructing a three-dimensional digital model of the knee joint and manufacturing a patient-specific alignment guide for the knee joint from the three-dimensional digital model of the knee joint when the plurality of two-dimensional images of the knee joint is sufficient to construct the three-dimensional digital model of the knee joint. The patient-specific alignment guide has a three-dimensional patient-specific surface pre-operatively configured to nest and closely conform to a corresponding surface of the knee joint of the patient in only one position relative to the knee joint. The method also includes determining, based on at least one of the two-dimensional images of the knee joint, a size of a non-custom implant to be implanted in the knee joint of the patient when there is insufficient image data to construct the patient-specific alignment guide therefrom. Additionally, the method includes determining a dimension for a non-custom surgical instrument configured for implanting the non-custom implant when there is insufficient image data to construct the patient-specific alignment guide therefrom. Moreover, the method includes manufacturing at least one of the non-custom implant and the non-custom surgical instrument when there is insufficient image data to construct the patient-specific alignment guide therefrom. Furthermore, the method includes assembling a kit containing the non-custom implant and the non-custom surgical instrument when there is insufficient image data to construct the patient-specific alignment guide therefrom.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although some of the present teachings are presented in relation to surgical planning for implanting a knee joint prosthesis, the present teachings can be employed for planning surgical implantation of any prosthetic device.

The present teachings provide various pre-operative planning methods for orthopedic procedures. For instance, the present teachings can be employed for planning partial or total knee joint replacement surgery. Specifically, image data from medical scans of the patient can be provided, and if there is sufficient two-dimensional image data, an accurate three-dimensional digital model of the knee joint can be generated as well as a three-dimensional digital model of a patient-specific alignment guide. If there is insufficient two-dimensional image data to generate the three-dimensional digital model and a patient-specific alignment guide therefrom, the image data can still be used to determine a size of a non-custom prosthesis to be implanted. The image data can also be used to determine sizes and dimensions for instruments (e.g., resection guides, etc.) that will be used during surgery. Moreover, a kit can be pre-operatively assembled containing the selected alignment guide(s), prosthetic device(s), trial prosthetic device(s), instruments, etc. that will be used during surgery for a particular patient. These methods can, therefore, make pre-operative planning more efficient. Also, the surgical procedure can be more efficient since the prosthetic device and the related surgical implements can be tailored for the particular patient.

Figure 1:
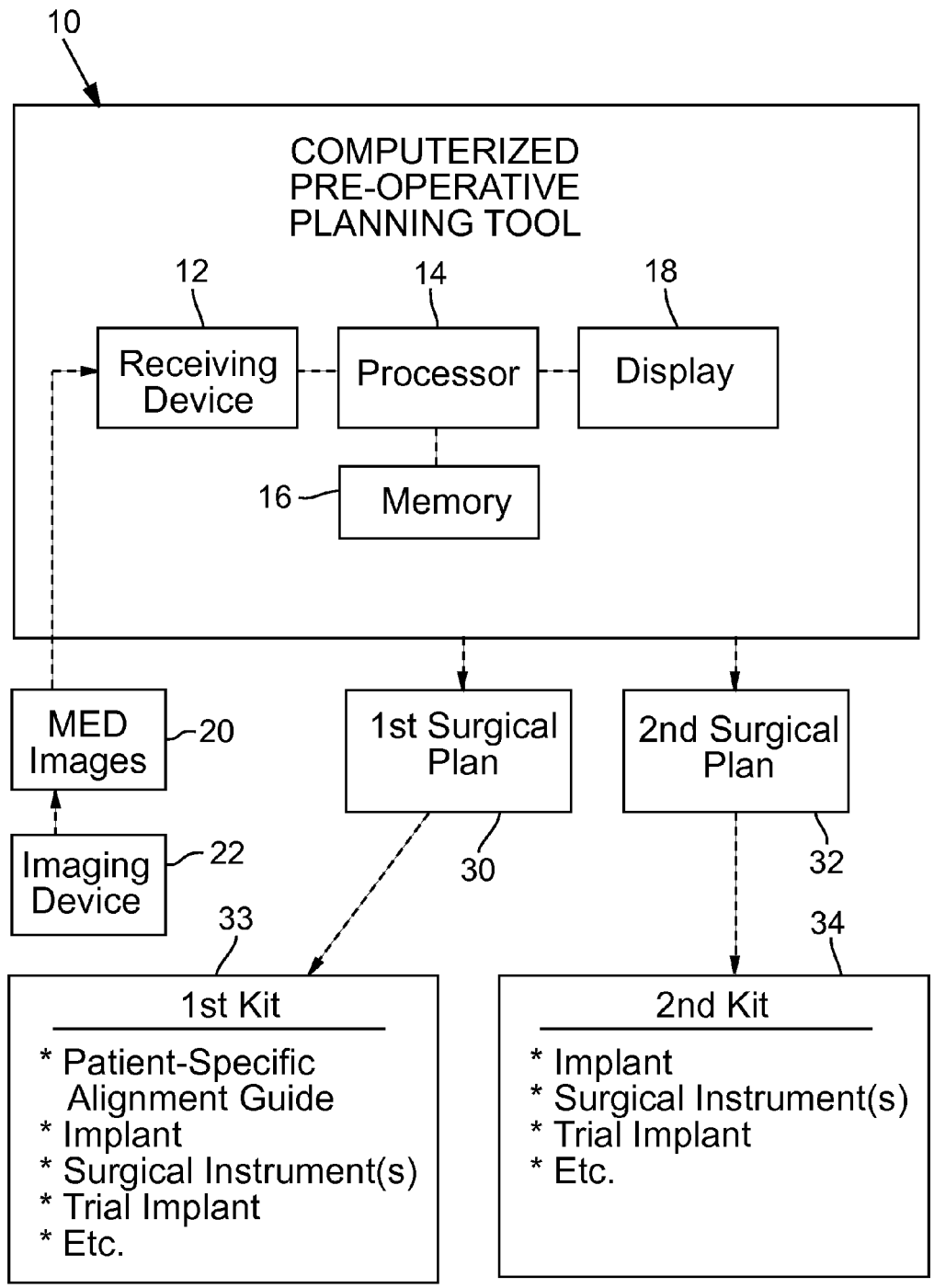
FIG. 1 is a schematic illustration of a pre-operative planning tool according to various exemplary embodiments of the present teachings.

Referring initially to FIG. 1, a pre-operative planning tool 10 is illustrated. The tool 10 can be computer-based and can generally include a receiving device 12, a processor 14, a memory device 16, and a display 18.

Figure 3:
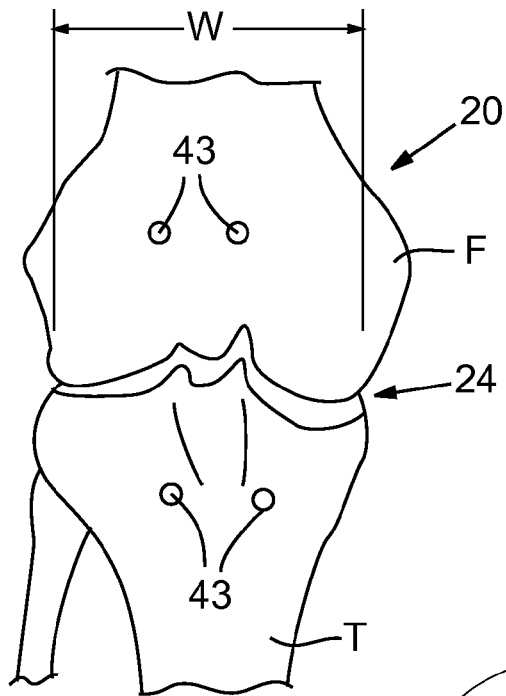
FIG. 3 is a two-dimensional image of a knee joint used in the pre-operative planning methods of the present teachings.

The receiving device 12 can receive medical image data 20 of a joint portion 24 (e.g., a knee joint) of a patient. Representative image data 20 of a knee joint portion 24 (including a femur F and a tibia T) of a patient is illustrated in FIG. 3. It will be appreciated that the image data 20 can include any number of images of the joint portion 24, taken from any viewing perspective.

Specifically, the receiving device 12 can receive medical scans prepared by a Magnetic Resonance Imaging (MRI) device, a Computed Tomography (CT) scanner, a radiography or X-ray machine, an ultrasound machine, a camera or any other imaging device 22. The imaging device 22 can be used to generate electronic (e.g., digital) image data 20. The image data 20 can be stored on a physical medium, such as a CD, DVD, flash memory device (e.g. memory stick, compact flash, secure digital card), or other storage device, and this data 20 can be uploaded to the tool 10 via a corresponding drive or other port of the receiving device 12. The image data 20 may alternatively, or in addition, be transmitted electronically to the receiving device 12 via the Internet or worldwide web using appropriate transfer protocols. Also, electronic transmissions can include e-mail or other digital transmission to any appropriate type of computer device, smart phone, PDA or other devices in which electronic information can be transmitted.

The memory device 16 can be of any suitable type (RAM and/or ROM), and the medical image data 20 can be inputted and stored in the memory device 16. The memory device 16 can also store any suitable software and programmed logic thereon for completing the pre-operative planning discussed herein. For instance, the memory device 16 can include commercially-available software, such as software from Materialise USA of Plymouth, Mich.

The processor 14 can be of a known type for performing various calculations, analyzing the data, and other processes discussed hereinbelow. Also, the display 18 can be a display of a computer terminal or portable device, such as an electronic tablet, or any other type of display. As will be discussed, the display 18 can be used for displaying the medical image data 20 and/or displaying digital anatomical models generated from the image data 20 and/or displaying other images, text, graphics, or objects.

It will also be appreciated that the pre-operative planning tool 10 can include other components that are not illustrated. For instance, the planning tool 10 can include an input device, such as a physical or electronic keyboard, a joystick, a touch-sensitive pad, or any other device for inputting user controls.

Figure 4A:
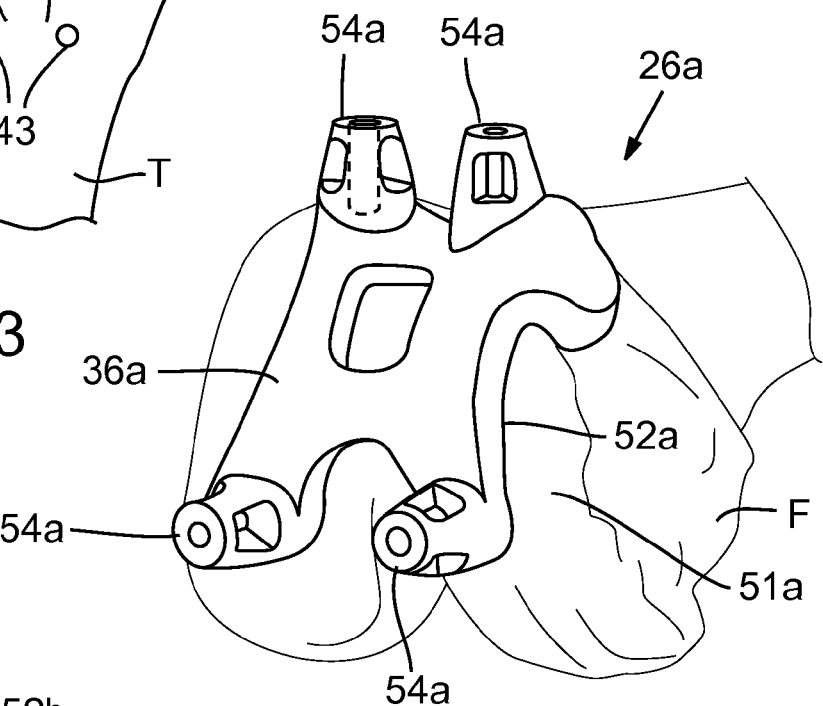
FIG. 4A is a three-dimensional digital model of a femur with a patient-specific alignment guide according to the present teachings.
Figure 4B:
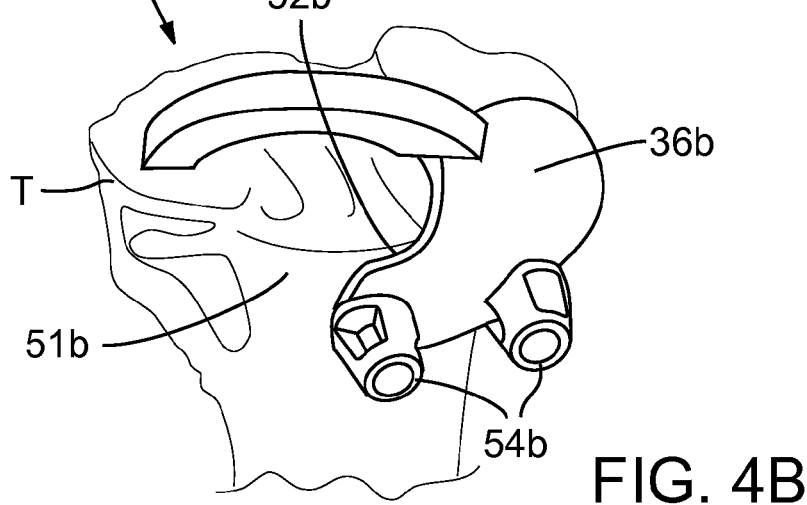
FIG. 4B is a three-dimensional digital model of a tibia with a patient-specific alignment guide according to the present teachings.

As will be discussed, the image data 20 can be analyzed and reviewed (manually or automatically) using the tool 10 to determine whether the image data 20 is sufficient enough to generate and construct a three-dimensional (3-d) digital model 26a, 26b of the joint 24. (A representative 3-d digital model 26a of the patient's femur F is illustrated in FIG. 4A, and a representative 3-d digital model 26b of the patient's tibia T is illustrated in FIG. 4B.)

For instance, if the image data 20 was collected by MRI or other higher-resolution imaging device, there are likely to be a relatively large number of two-dimensional images of the joint 24 taken at different anatomical depths, and these images can be virtually assembled ("stacked") by the processor 14 to generate the three-dimensional electronic digital model 26a, 26b of the patient's anatomy. Using these digital models 26a, 26b, a first surgical plan 30 (FIG. 1) can be generated, and a corresponding kit 33 can be manufactured and assembled. As will be discussed, the kit 33 can include the physical components necessary for surgery, including patient-specific alignment guide(s), selected prosthetic devices, trial prosthetic devices, surgical instruments, and more. The kit 33 can be sterilized and shipped to be available for surgery for that particular patient.

However, if the image data 20 was collected by X-ray or other lower-resolution imaging device, there is unlikely to be sufficient data about the joint 24 to generate accurate three-dimensional digital models 26a, 26b. Regardless, the two-dimensional image data 20 can still be used to generate a second surgical plan 32 as shown in FIG. 1, and a corresponding kit 34 can be assembled. The kit 34 can include a selected non-patient-specific (non-custom) implant, trial implant, surgical instruments, and more. However, the items within the kit 34 can be size-specific (i.e., the size of the items in the kit 34 can be pre-operatively selected for the particular patient).

It will be appreciated that the same tool 10 can be used for planning purposes, regardless of whether the image data 20 is sufficient to generate three-dimensional digital models of the joint 24 or not. Thus, for instance, if the patient is able and willing to undergo MRI to obtain highly detailed images as recommended by the surgeon, the tool 10 can be used to generate a surgical plan 30 and to manufacture implements that are highly customized for that patient. Otherwise, if the patient is unable or unwilling to undergo MRI (e.g., because the patient has a pacemaker, because the patient has claustrophobia, because MRI is not recommended by the surgeon, etc.), the tool 10 can still be used to generate the surgical plan 32, albeit with implements that are selected from inventory or manufactured on a non-custom basis. In either case, the surgery can be planned and carried out efficiently.

Figure 2:
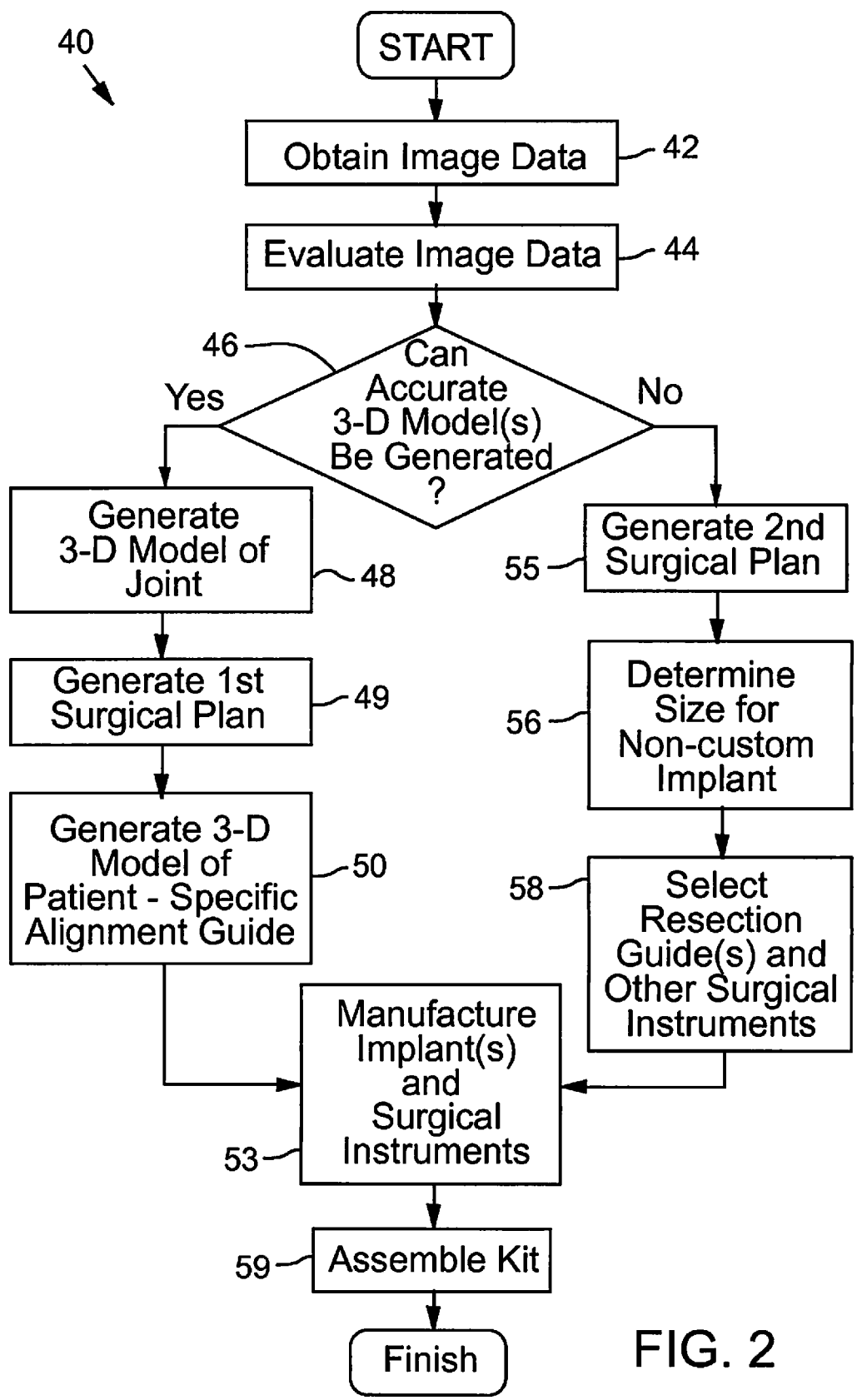
FIG. 2 is a flowchart of a method of a pre-operative planning and manufacturing method according to various exemplary embodiments of the present teachings.

Referring now to FIG. 2, a method 40 of using the tool 10 will be discussed. The method 40 can begin in block 42, in which the image data 20 is obtained. As mentioned above, the image data 20 can be obtained from an MRI device, an X-ray device, or the like. In the case of data 20 obtained by X-ray, one or more radio-opaque (e.g., magnetic) markers or scaling devices 43 can be used as shown in FIG. 3. These devices 43 can be of a known size and shape. For instance, the devices 43 can be discs that measure ten centimeters in diameter, or the devices 43 can be elongate strips or other shapes with known dimensions. The devices 43 can be placed over the patient's knee joint 24 before the X-ray is taken. The devices 43 will be very visible in the X-ray image. Since the actual size of the devices 43 are known, the size of the device 43 can be compared against the anatomical measurements taken from the image, and the scale of anatomy in the image can be thereby detected.

Next, as shown in FIG. 2, the method 40 can continue in block 44, in which the image data 20 can be evaluated, and in block 46, it can be determined whether there is enough data to generate accurate 3-d digital model(s) 26a, 26b of the joint 24. "Accurate" in this context means that the image data 20 is sufficient and detailed enough to generate precise representations of the anatomical joint 24. More specifically, "accurate 3-d models" are those that are detailed and precise enough to construct a patient-specific alignment guide therefrom. (Patient-specific alignment guides will be discussed in greater detail below.) It is noted that three 3-d models can still be generated from a lesser or insufficient number of medical scans, although such 3-d models will not be accurate enough to generate patient-specific alignment guides that mirror the corresponding joint surfaces of the specific patients.

In some embodiments, the processor 14 can analyze the data 20 to automatically determine if it is sufficient to model the complex, three-dimensionally curved surfaces of the distal end of the femur F and the proximate end of the tibia T. In other embodiments, the tool 10 can automatically detect whether the data 20 is MRI data (higher-resolution data) or X-ray data (lower-resolution data). If the data 20 is MRI data, then the digital models 26a, 26b can be generated and block 46 is answered affirmatively. If the data 20 is X-ray data, then the digital models 26a, 26b cannot be generated and block 46 is answered negatively.

If decision block is answered in the affirmative, then block 48 follows, and the digital models 26a, 26b are generated as represented in FIGS. 4A and 4B. These digital models 26a, 26b can be displayed on the display 18. Subsequently in block 49, the first surgical plan 30 is generated. Specifically, various dimensions of the femur F and tibia T can be automatically detected from the digital models 26a, 26b, the mechanical axis of the joint 24 can be detected from the digital models 26a, 26b, resection plane(s) for the femur F and tibia T can be planned according to the digital models 26a, 26b, soft tissue can be analyzed in the digital models, etc. A prosthetic implant assembly 60 (FIG. 6) can then be selected and/or designed according to this analysis.

Figure 6:
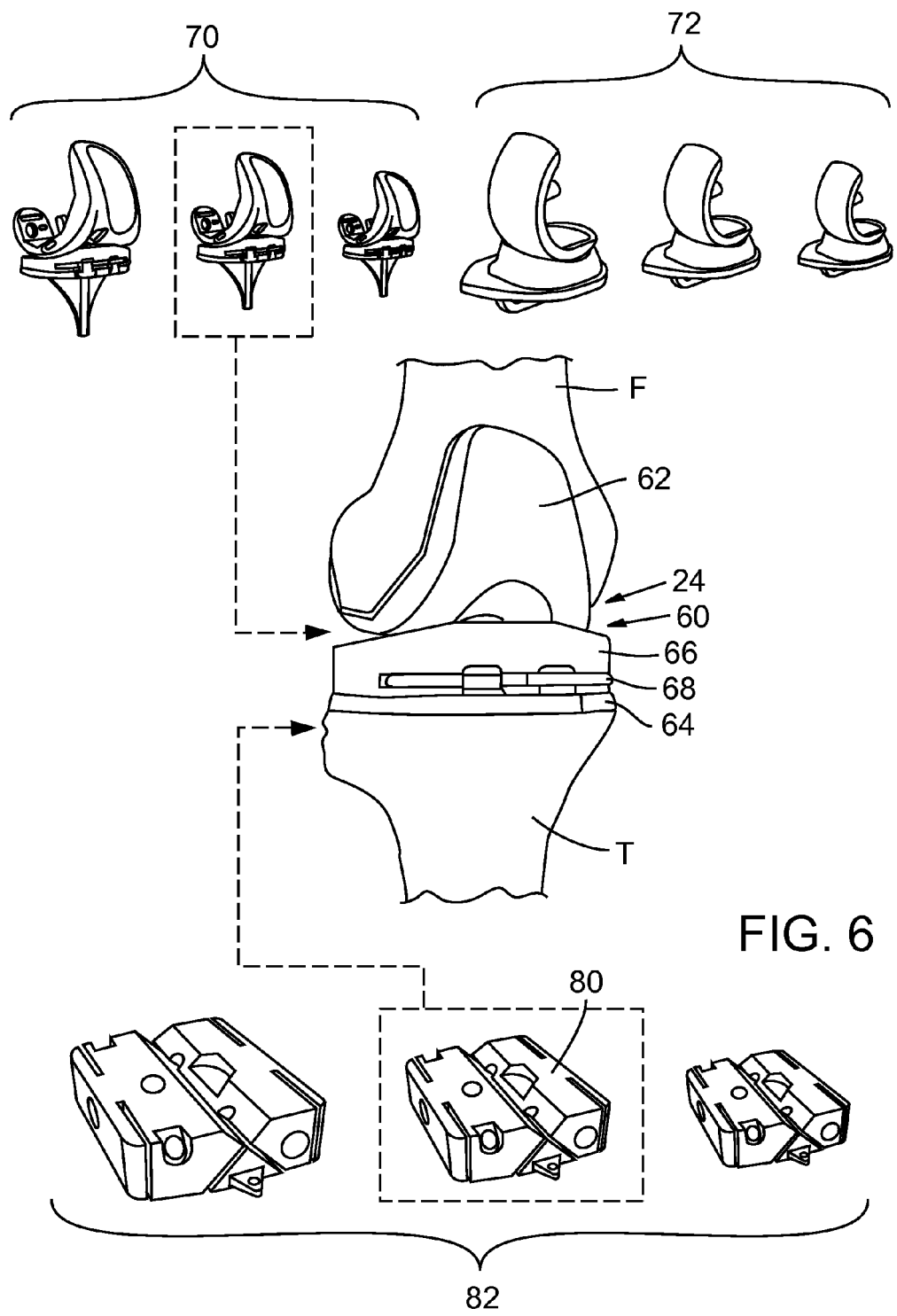
FIG. 6 is a schematic illustration of a kit containing components for implanting a knee prosthesis.

More specifically, as shown in FIG. 6 various inventories 70, 72 of differently sized prosthetic implant assemblies 60 can be provided. The inventory 70 can include components for a full knee replacement, and the inventory 72 can include components for a partial knee replacement. From the digital models 26a, 26b, the surgeon can decide to do a full knee replacement, as represented in FIG. 6. From the digital models 26a, 26b, the surgeon can also determine the size of the prosthetic implant assembly 60 that is appropriate for the patient. Thus, the surgeon can determine the size and other appropriate features for a femoral component 62, a tibial component 64 (tibial tray), a bearing 66, and one or more fasteners 68 for the patient. Each of these components 62, 64, 66, 68 can be individually selected from the inventory 70.

In some embodiments, the prosthetic implant assembly 60 can be selected from non-custom, inventoried components of the commercially-available VANGUARD™ complete knee system of Biomet, Inc. of Warsaw, Ind. The surgeon also has the option of selecting components from the other inventory 72, such as partial knee prosthetic implants of the OXFORD™ partial knee system of Biomet, Inc. of Warsaw, Ind. In still other cases, the surgeon can design a patient-specific prosthetic implant (i.e., one that is customized, non-inventoried, and intended for a single patient). In any case, the surgeon can rely on the digital models 26a, 26b for selecting and/or designing the most appropriate implant assembly 60 for restoring function of the joint 24. It will be appreciated that the prosthetic implant assembly 60 can be selected from any one of various types, such as bilateral or unilateral implants, constrained, semi-constrained, mobile types, etc. It will also be appreciated that the components 62, 64, 66, 68 may not be stocked in inventory, and the components 62, 64, 66, 68 can be manufactured on-demand.

A resection guide 80 can also be selected from an inventory 82 of different resection guides of different sizes and dimensions. The resection guide 80 can include one or more guide surfaces (e.g., grooves, or slots) used for guiding a resection tool while resecting the bones F, T. The resection guide 80 can be selected such that the resection plane(s) will be located as determined in block 49. The resection guide 80 can be of any suitable type, such as a 4-in-1 femoral cut block, which is commercially available from Biomet, Inc. of Warsaw, Ind. Resection guides can also be selected for resecting the tibia T as well.

Once the surgical plan has been generated in block 49, block 50 follows as shown in FIG. 2. In block 50, patient-specific alignment guides 36a, 36b (FIGS. 4A and 4B) can be designed according to the anatomical digital models 26a, 26b and according to the prosthetic implant assembly 60 selected in block 49. Patient-specific alignment guides 36a, 36b and their method of manufacture are disclosed and described in detail in the commonly-owned, co-pending U.S. patent application Ser. No. 11/756,057, filed on May 31, 2007, and published as U.S. Patent Publication No. 2007/0288030, which is hereby incorporated herein by reference in its entirety. The femoral alignment guide 36a can be configured to include a three-dimensional patient-specific surface 52a that nests and closely conforms to a corresponding surface 51a of the distal femur F in only one position (with or without articular cartilage). Likewise, the tibial alignment guide 36b can be configured to include a three-dimensional patient-specific surface 52b that nests and closely conforms to a corresponding surface 51b of the proximal tibia T in only one position (with or without articular cartilage). Furthermore, the alignment guides 36a, 36b can each be designed to include respective alignment holes 54a, 54b at predetermined locations relative to the bones F, T. The alignment holes 54a, 54b can be positioned relative to the bones F, T for aligning surgical instruments (drill guides, resection guides, etc.).

Next, in block 53, the alignment guides 36a, 36b can be manufactured. The digital models 26a, 26b can be used to automatically generate computer instructions of tool paths for machining the patient-specific alignment guide(s) 36a, 36b. These instructions can be stored in a tool path data file and provided as input to a CNC mill or other automated maching system, and the alignment guides 36a, 36b can be machined from polymer, ceramic, metal or other suitable material, and sterilized. The sterilized alignment guides 36a, 36b can be shipped to the surgeon or medical facility for use during the surgical procedure. The alignment guides 36a, 36b can also be manufactured out of a polymer or other material using known rapid-prototyping machines and techniques. Also, in block 53, the components of the prosthetic implant assembly 60 selected in block 49 can be manufactured. These components can be made from a biologically compatible material (e.g., Titanium), and can be manufactured by casting and polishing manufacturing methods. In other embodiments, the method 40 can skip block 53 because the prosthetic implant assembly 60 has been previously manufactured and the assembly 60 is simply obtained from inventory. Trial prosthetics (e.g., prosthetic components that are temporarily implanted as a test during surgery) can also be manufactured in block 53.

Finally, in block 59, the kit 33 containing all of the previously-selected components is assembled for the particular patient. As mentioned above with respect to FIG. 1, the kit 33 can include the patient-specific alignment guides 36b, the prosthetic implant assembly 60 selected in block 49, trial prosthetics, resection guides and other instruments, etc. The kit 33 can be sterilized and shipped to the surgeon or surgical facility for surgery. Accordingly, the planning tool 10 and its method 40 of use can be highly effective for tailoring the surgery to the particular patient, and the proper components are very likely to be available during surgery.

Figure 5:
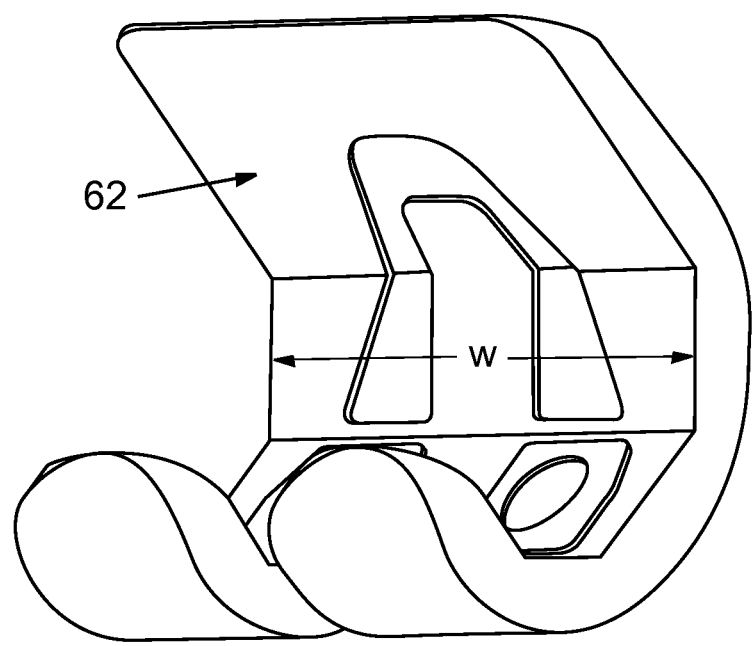
FIG. 5 is an isometric view of a femoral component of a knee prosthesis.

Referring back to block 46, if the image data 20 is insufficient for generating an accurate 3-d digital models (i.e., block 46 answered negatively), then block 55 follows, and the second surgical plan 32 is generated according to the available 2-d image data 20. The image data 20 can be displayed on the display 18. Next, in block 56, the anatomy can be measured in order to select a non-custom implant that would be appropriate for the particular patient. For instance, as shown in FIG. 3, a condylar width W can be measured directly from the image data 20, and as shown in FIG. 5, a femoral component 62 with a width W closest to the measured width W can be selected from inventory 70 (FIG. 6) for implantation. Other anatomical dimensions and features of the anatomy can be similarly measured to identify the appropriate femoral component 62 for implantation. The tibia T can be similarly measured to identify the appropriate tibial component 64 and bearing 66. In some embodiments, 2-d templates can be generated and utilized according to the image data 20, and these templates can be used for selecting the components of the prosthetic implant assembly 60.

Subsequently, in block 58, a resection guide 80 can be selected from an inventory 82 of different resection guides of different sizes and dimensions. The resection guide 80 can be selected such that the resection plane(s) will be located as determined in block 55. The resection guide 80 can be of any suitable type, such as a 4-in-1 femoral cut block, which is commercially available from Biomet, Inc. of Warsaw, Ind. Resection guides can also be selected for resecting the tibia T as well. Other resection guides, including distal femoral cutting blocks, and/or other surgical instruments (drill guides, etc.) can be selected in a similar fashion in block 58.

Next, the components of the non-custom prosthetic implant assembly 60 can be manufactured in block 53. Alternatively, as discussed above, the components can be retrieved from inventory. Finally, the kit 34 containing the components of the implant assembly 60, a trial implant, surgical instruments can be assembled in block 59 and stored until the day of surgery.

In summary, the methods described above can streamline pre-operative planning because the surgery can be planned based on either 2-d or 3-d medical image data 20. The surgery, the prosthetic implant assembly 60 and surgical instruments can be tailored for the particular patient in an efficient and convenient fashion.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A pre-operative planning and manufacturing method for orthopedic surgery comprising:
    obtaining pre-operative medical image data representing a joint portion of a patient;
    constructing a three-dimensional digital model of the joint portion and manufacturing a patient-specific alignment guide for the joint portion from the three-dimensional digital model of the joint portion when the image data is sufficient to construct the three-dimensional digital model of the joint portion, the patient-specific alignment guide having a three-dimensional patient-specific surface pre-operatively configured to nest and closely conform to a corresponding surface of the joint portion of the patient in only one position relative to the joint portion; and
    determining, from the image data, a size of a non-custom implant to be implanted in the patient and manufacturing the non-custom implant when there is insufficient image data to construct the patient-specific alignment guide therefrom.

2. The method of claim 1, further comprising manufacturing a patient-specific implant after constructing the three-dimensional digital model of the joint portion.

3. The method of claim 1, wherein determining the size of the non-custom implant includes selecting the non-custom implant from a group of non-custom implants of different sizes.

4. The method of claim 1, further comprising determining, from the image data, a dimension of a non-custom surgical instrument configured for use during surgery for implanting the non-custom implant.

5. The method of claim 4, wherein the non-custom surgical instrument is a resection tool with a guide surface configured for guiding a cutting tool during resection of a bone of the joint portion.

6. The method of claim 4, further comprising selecting the non-custom surgical instrument from a plurality of non-custom surgical instruments of different dimensions.

7. The method of claim 1, further comprising manufacturing a trial implant that corresponds to the non-custom implant.

8. The method of claim 1, further comprising assembling a kit containing the non-custom implant, a non-custom surgical instrument configured for use during surgery for implanting the non-custom implant, and a trial implant that corresponds to the non-custom implant.

9. The method of claim 1, wherein the joint portion is a knee joint and the non-custom implant is at least one of a femoral implant and a tibial implant.

10. A pre-operative planning and manufacturing method for orthopedic surgery comprising:
pre-operatively obtaining medical image data that is readable on a computer, the medical image data containing a plurality of two-dimensional medical images of a joint portion of a patient;
pre-operatively constructing a three-dimensional digital model of the joint portion from the plurality of two-dimensional medical images and displaying the three-dimensional digital model on a display of the computer when the plurality of two-dimensional medical images are sufficient to construct the three-dimensional digital model of the joint portion and a corresponding a patient-specific alignment guide; and
selecting, based on the image data, a non-custom implant to be implanted in the patient and providing the non-custom implant when the plurality of two-dimensional medical images are insufficient for use in constructing a patient-specific alignment guide having a three-dimensional patient-specific surface configured to nest and closely conform to a corresponding surface of the joint portion of the patient in only one position relative to the joint portion, the non-custom implant chosen from a group of non-custom implants of different sizes.

11. The method of claim 10, further comprising manufacturing the patient-specific alignment guide when the plurality of two-dimensional medical images are sufficient, the patient-specific alignment guide having a three-dimensional patient-specific surface pre-operatively configured to nest and closely conform to a corresponding surface of the joint portion of the patient in only one position relative to the joint portion, and further comprising manufacturing the selected non-custom implant when the plurality of two-dimensional medical images are insufficient to construct the patient-specific alignment guide therefrom.

12. The method of claim 10, further comprising manufacturing a patient-specific implant after constructing the three-dimensional digital model of the joint portion.

13. The method of claim 10, further comprising determining, from the medical image data, a dimension of a non-custom surgical instrument configured for use during surgery for implanting the non-custom implant.

14. The method of claim 13, wherein the non-custom surgical instrument is a resection tool with a guide surface configured for guiding a cutting tool during resection of a bone of the joint portion.

15. The method of claim 13, further comprising selecting the non-custom surgical instrument from a plurality of non-custom surgical instruments of different dimensions.

16. The method of claim 10, further comprising manufacturing a trial implant that corresponds to the non-custom implant.

17. The method of claim 10, further comprising assembling a kit containing the non-custom implant, a non-custom surgical instrument configured for use during surgery for implanting the non-custom implant, and a trial implant that corresponds to the non-custom implant.

18. The method of claim 10, wherein the joint portion is a knee joint and the non-custom implant is at least one of a femoral implant and a tibial implant.

19. A computerized pre-operative planning tool for planning an orthopedic surgical procedure comprising:
a receiver device that receives medical image data containing a plurality of two-dimensional medical images of a joint portion of a patient;
a processor that determines whether the medical image data is sufficient for constructing a three-dimensional digital model of the joint portion from the plurality of two-dimensional medical images, the processor also configured to construct the three-dimensional digital model when the medical image data is sufficient to construct the three-dimensional digital model, the processor further configured to construct a patient-specific digital model of a patient-specific alignment guide when the medical image data is sufficient to construct the three-dimensional digital model, the patient-specific alignment guide having a three-dimensional surface that nests against a corresponding surface of the three-dimensional digital model of the joint portion; and
a display that displays the three-dimensional digital model of the joint portion and the patient specific digital model of the patient-specific alignment guide when the processor determines that the medical image data is sufficient for constructing the three-dimensional digital model of the joint portion, the display also displaying at least one of the two-dimensional medical images of the joint portion for selection of a non-custom implant when the processor determines that the medical image data is insufficient for constructing the patient-specific alignment guide therefrom.

20. A pre-operative planning and manufacturing method for orthopedic surgery of a knee joint of a patient comprising:
obtaining pre-operative medical image data representing the knee joint, the medical image data including a plurality of two-dimensional images of the knee joint;
constructing a three-dimensional digital model of the knee joint and manufacturing a patient-specific alignment guide for the knee joint from the three-dimensional digital model of the knee joint when the plurality of two-dimensional images of the knee joint is sufficient to construct the three-dimensional digital model of the knee joint, the patient-specific alignment guide having a three-dimensional patient-specific surface pre-operatively configured to nest and closely conform to a corresponding surface of the knee joint of the patient in only one position relative to the knee joint;
determining, based on at least one of the two-dimensional images of the knee joint, a size of a non-custom implant to be implanted in the knee joint of the patient when there is insufficient image data to construct the patient-specific alignment guide therefrom;
determining a dimension for a non-custom surgical instrument configured for implanting the non-custom implant when there is insufficient image data to construct the patient-specific alignment guide therefrom;
manufacturing at least one of the non-custom implant and the non-custom surgical instrument when there is insufficient image data to construct the patient-specific alignment guide therefrom; and
assembling a kit containing the non-custom implant and the non-custom surgical instrument when there is insufficient image data to construct the patient-specific alignment guide therefrom.

* * * * *